(12) United States Patent
Radhakrishnan et al.

(10) Patent No.: US 6,953,856 B2
(45) Date of Patent: *Oct. 11, 2005

(54) PROCESS FOR THE PREPARATION OF 1-BENZYL-4-(5,6-DIMETHOXY-1-INDANON)-2-YL) METHYL PIPERIDINE HYDROCHLORIDE (DONEPEZIL HCl)

(75) Inventors: Tarur Venkatasubramanian Radhakrishnan, Maharashtra (IN); Sathe Dhanajay Govind, Maharashtra (IN); Naidu Avinash Venkatraman, Maharashtra (IN)

(73) Assignee: USV, Limited, Mumbai (IN)

( * ) Notice: Subject to any disclaimer, the term of this patent is extended or adjusted under 35 U.S.C. 154(b) by 1 day.

This patent is subject to a terminal disclaimer.

(21) Appl. No.: 10/714,724

(22) Filed: Nov. 17, 2003

(65) Prior Publication Data

US 2004/0158070 A1 Aug. 12, 2004

Related U.S. Application Data

(63) Continuation-in-part of application No. 10/365,717, filed on Feb. 12, 2003, now Pat. No. 6,649,765.

(51) Int. Cl.$^7$ .................... C07D 211/02; C07D 211/06
(52) U.S. Cl. ........................................ 546/185; 546/206
(58) Field of Search ................. 546/185, 206

(56) References Cited

U.S. PATENT DOCUMENTS

| 4,895,841 A | 1/1990 | Sugimoto et al. |
| 5,606,064 A | 2/1997 | Lensky |
| 6,252,081 B1 | 6/2001 | Iimura |

FOREIGN PATENT DOCUMENTS

WO     WO 97/22584     6/1997

*Primary Examiner*—Ceila Chang
*Assistant Examiner*—Raymond Covington
(74) *Attorney, Agent, or Firm*—Pharmaceutical Patent Attorneys, LLC

(57) ABSTRACT

A process for the preparation of 1-benzyl-4-[(5,6-dimethoxy-1-indanon)-2-yl] methyl piperidine hydrochloride (Donepezil HCl) is disclosed. 5,6-Dimethoxy-2-(pyridin-4-yl) methylene inda-1-one is hydrogenated with a noble metal catalyst or a non-oxide derivative of a noble metal catalyst in a solvent at 20–100° C. and 10–90 psi gauge pressure. The resulting 4-[(5,6-dimethoxy-1-indanon)-2-yl] methyl piperidine is alkylated with an alkylating agent in an organic solvent at 20–80° C.

16 Claims, No Drawings

PROCESS FOR THE PREPARATION OF 1-BENZYL-4-(5,6-DIMETHOXY-1-INDANON)-2-YL) METHYL PIPERIDINE HYDROCHLORIDE (DONEPEZIL HCl)

CROSS-REFERENCE TO RELATED APPLICATIONS

This application is continuation-in-part of U.S. application Ser. No. 10/365,717, filed Feb. 12, 2003 now U.S. Pat. No. 6,649,765, which is entirely incorporated herein by reference.

BACKGROUND OF THE INVENTION

1. Field of the Invention

This invention relates to a process for the preparation of 1-benzyl-4-[(5,6-dimethoxy-1-indanon)-2-yl] methyl piperidine hydrochloride (Donepezil HCl) of the formula 1.

Formula 1

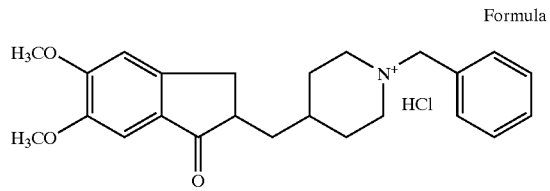

Compound of the formula 1 commonly known as Donepezil HCl is used for treatment of Central Nerve System (CNS) disorders.

2. Description of the Related Art

U.S. Pat. No. 4,895,841 describes preparation of Donepezil HCl by reacting 5,6-dimethoxy-1-indanone with 1-benzyl-4-formylpiperidine in the presence of a strong base such as lithium diisopropyl amide followed by reduction with palladium carbon catalyst (Examples 3 and 4). Overall yield of Donepezil HCl is reported to be 50.8% (62%×82%).

U.S. Pat. No. 5,606,064 teaches the preparation of Donepezil HCl by the reaction of 5,6-dimethoxy-1-indanone with pyrindin-4-aldehyde. The resulting 5,6-dimethoxy-2-(pyridin-4-yl)methyleneinda-1-one is reacted with benzyl bromide to afford 1-benzyl-4-[(5,6-dimethoxy-1-indanon-2-ylidene] methyl pyridinium bromide which on reduction with platinum oxide catalyst afforded Donepezil HCl. (Examples 2, 4 and 6). Overall yield of Donepezil HCl 58.5% (87%×83%×81%).

PCT Publication No. WO 97/22584 reports preparation of Donepezil HCl by reacting pyridine-4-aldehyde with malonic acid. The resulting 3-(pyridin-4-yl)-2-propionic acid was reduced with rhodium on carbon under hydrogen atmosphere to give 3-(piperidin-4-yl)-2-propionic acid which on reaction with methyl chlorocarbonate gave 3-[N-(methoxycarbonyl)piperidin-4-yl]propionic acid. On reacting 3-[N-(methoxycarbonyl) piperidin-4-yl] propionic acid with oxalyl chloride, methyl 4-(2-chlorocarbonylethyl) piperidin-1-carboxylate is obtained which on reaction with 1,2-dimethoxy benzene in the presence of aluminum chloride afforded 4-[3-(3,4-dimethoxyphenyl)-3-oxopropyl] piperidin-1-carboxylate. On reacting 4-[3-(3,4-dimethoxyphenyl)-3-oxopropyl] piperidin-1-carboxylate with tetramethyl diamino methane, 4-[2-(3,4-dimethoxy benzoyl) allyl] piperidin-1-carboxylate is obtained which on treatment with sulphuric acid gave methyl 4-(5,6-dimethoxy-1-indanon-2-yl methyl)piperidin-1-carboxylate. On decarboxylating 4-(5,6-dimethoxy-1-indanon-2-yl methyl) piperidin-1-carboxylate, 5,6-dimethoxy-2-(piperidin-4-yl methyl)-1-indanone is obtained which on treatment with benzyl bromide afforded Donepezil HCl (Example 1 to 6). Overall yield of Donepezil HCl 19.3% (70%×84%×100%×68%×79%×61%).

U.S. Pat. No. 6,252,081 teaches the preparation of Donepezil HCl by the reaction of 1-indanone derivative with carbonate ester. The resulting 2-alkoxycarbonyl-1-indanone derivative is halogenated with (4-pyridyl) methyl or a salt thereof and decarboxylated successively to give 2-(4-pyridyl)methyl-1-indanone derivative. On reacting the 2-(4-pyridyl) methyl-1-indanone derivative with benzyl bromide, their quaternary ammonium salts are formed, which on reduction with platinum oxide catalyst gives Donepezil HCl (Examples 1 to 3). Overall yield of Donepezil HCl 82% (98%×85%×100%×99%).

The prior art processes employs 1-benzyl-4-formyl piperidine as starting material whose synthesis is low yielding and involves use of lithium diisopropyl amide. The reaction of 1-benzyl-4-formyl piperidine with 5,6-dimethoxy-1-indanone also involves use of lithium diisopropyl amide and cryogenic temperatures which are expensive and are not economically viable. Lithium diisopropyl amide is toxic and needs to be carefully handled. Many a time selective reduction of double bond to yield 1-benzyl-4-[(5,6-dimethoxy-1-indanon)-2-yl] methyl piperidine hydrochloride is difficult to achieve. Besides, the selective reduction of double bond to give 1-benzyl-4-[(5,6-dimethoxy-1-indanon)-2-yl] methyl piperidine hydrochloride is many a time coupled with formation of side products which are difficult to separate. Yield of the product is also affected due to the formation of the side products. Use of oxalyl chloride chemistry is difficult for scale up. Besides the oxalyl reaction also involves many protection deprotection chemistry and the overall yield is very low. Raw materials like methyl chlorocarbonate or tetramethyl diaminomethyl are expensive and difficult to source commercially. The prior art processes are also time consuming and difficult to carry out as they involve many steps.

SUMMARY OF THE INVENTION

One embodiment is to provide a process for the preparation of 1-benzyl-4-[5,6-dimethoxy-1-indanon)-2-yl] methyl piperidine hydrochloride which eliminates formation of byproducts and gives high yield of the product and is efficient and economical.

Another embodiment is to provide a process for the preparation of 1-benzyl-4-[(5,6-dimethoxy-1-indanon)-2-yl] methyl piperidine hydrochloride which employs less number of reaction steps and is less time consuming and easy and convenient to carry out.

Another embodiment is to provide a process for the preparation of 1-benzyl-4-[(5,6-dimethoxy-1-indanon)-2-yl] methyl piperidine hydrochloride which eliminates use of hazardous reagents and is safe to carryout.

Another embodiment is to provide a process for the preparation of 1-benzyl-4-[(5,6-dimethoxy-1-indanon)-2-yl] methyl piperidine hydrochloride which employs cheaper and easily available raw materials.

Another embodiment is to provide a process for the preparation of 1-benzyl-4-[(5,6-dimethoxy-1-indanon)-2-yl] methyl piperidine hydrochloride which is suitable for industrial scale up.

DETAILED DESCRIPTION OF THE PREFERRED EMBODIMENT

According to an embodiment, there is provided a process for the preparation of 1-benzyl-4-[(5,6-dimethoxy-1- indanon)-2-yl] methylpiperidine hydrochloride (Donepezil HCl) of the formula I

Formula I

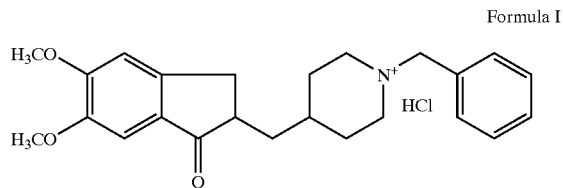

comprising hydrogenating 5,6-dimethoxy-2-(pyridin-4-yl) methylene inda-1-one with a noble metal oxide catalyst in an organic solvent at 20–50° C. and 10–45 psi gauge pressure to form 4-[(5,6-dimethoxy-1-indanon)-2-yl] methyl piperidine of the formula II Formula II

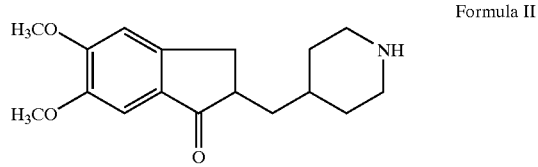

which is alkylated with an alkylating agent in an organic solvent at 20–80° C.

According to another embodiment, there is also provided a process for the preparation of 1-benzyl-4-[(5,6-dimethoxy-1-indanon)-2-yl] methylpiperidine hydrochloride (Donepezil HCl ) of the formula I Formula I

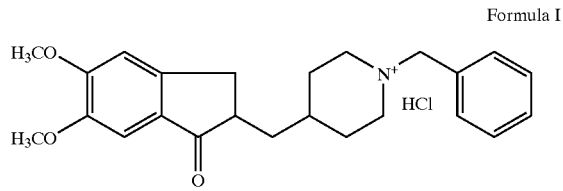

comprising hydrogenating 5,6-dimethoxy-2-(pyridin-4-yl) methylene indan-1-one with a noble metal catalyst or a non-oxide derivative of a noble metal catalyst in a solvent at 20–100° C. and 10–90 psi gauge pressure to form 4-[(5,6-dimethoxy-1-indanon)-2-yl] methyl piperidine of the Formula II Formula II

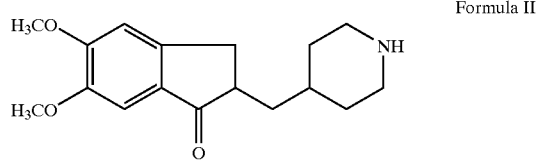

which is alkylated with an alkylating agent in an organic solvent at 20–80° C.

The organic solvent used in the hydrogenation of compound of the formula II with a noble metal oxide catalyst may be tetrahydrofuran, methanol or acetic acid or combination thereof preferably acetic acid:methanol mixture. Suitable solvents used in the hydrogenation of compound of the formula II with a noble metal catalyst or a non-oxide derivative of a noble metal catalyst may be $C_1$–$C_4$ aliphatic alcohol, organic acid, dilute HCl, ethyl acetate, aliphatic ketone, or mixtures thereof. Preferably, the suitable solvent used with a noble metal catalyst or a non-oxide derivative of a noble metal catalyst is acetic acid.

The noble metal oxide catalyst used in hydrogenation may be platinum or palladium oxide, preferably platinum dioxide.

A noble metal catalyst used in hydrogenation may be palladium, rhodium, or ruthenium metal. A non-oxide derivative of a noble metal catalyst may also be used, such as a chloride or a sulphate of a noble metal selected from the group consisting of palladium, rhodium, and ruthenium.

The noble metal catalyst or non-oxide derivative of a noble metal catalyst can be supported on a carrier, such as carbon, calcium carbonate, barium sulphate, or alumina. A preferred carrier is carbon.

A preferred noble metal catalyst is palladium. A preferable condition for hydrogenation with a noble metal catalyst is 10% concentration of palladium on carbon.

Preferably hydrogenation using a noble metal oxide catalyst is carried out at 25–40° C. and 25–40 psi gauge. Preferably hydrogenation using a noble metal catalyst or a non-oxide derivative of a noble metal catalyst is carried out at 70–80° C. and 45–55 psi gauge. Preferably hydrogenation using a noble metal catalyst or a non-oxide derivative of a noble metal catalyst is carried out at about 75° C. and about 50 psi gauge.

The alkylating agent may be benzyl bromide or benzyl chloride, preferably benzyl bromide.

The organic solvent used in the alkylation reaction may be methylenedichloride, triethyl amine or mixtures thereof preferably methylene dichloride and triethyl amine mixture.

Preferably the alkylation is carried out at 20–80° C., more preferably at 30–40° C.

The process of preferred embodiments eliminates formation of byproducts and gives high yield of the product (about 92%). It employs cheaper and easily available raw materials and eliminates use of hazardous reagents. It is, therefore, efficient and economical and safe to carryout. It comprises only two steps and is, therefore, less time consuming and is easy and convenient to carryout. For the above reasons, it is also suitable for industrial scale up.

The following examples are illustrative of the invention but not limitative of the scope thereof.

EXAMPLE 1

4-[5,6-dimethoxy-1-indanon)-2-yl] methyl piperidine 10 g (0.035 mole) 5,6-dimethoxy-2-(pyridin-4-yl) methylene indan-1-one and 1 g Platinum dioxide were suspended in acetic acid-methanol mixture (200 ml: 200 ml) at room temperature and 30 psi gauge for six hours. Platinum dioxide was filtered off and the filtrate was concentrated. The residue was treated with 10% sodium hydrogen carbonate solution and the solution was extracted three times with methylene dichloride, dried and concentrated. Yield 10.1 g (99%). Corresponding HCl, mp 248–250° C., lit. mp 249–250° C., $^1$H NMR (base, 200 MHz CDCl$_3$) δ (ppm) 7.1 (s, 1H), 6.9 (s, 1H), 3.9 (s, 1H), 3.8 (s, 3H), 3.0–3.2 (m, 3H), 2.6–2.7 (m, 4H), 2.2 (bs, 1H, exchanges with D$_2$O), 1.6–1.7 (m, 4H), 1.2–1.3 (m, 3H).

EXAMPLE 2

1-benzyl-4-[(5,6-dimethoxy-1-indanon)-2-yl) methyl piperidine hydrochloride 10 g (0.0346 mol) of 4-[(5,6-dimethoxy-1-indanon)-2-yl] methyl piperidine was dissolved in 100 ml methylene dichloride followed by 6.5 g benzyl bromide and 13 g triethyl amine. The reaction mixture was refluxed for four hours. The reaction mixture was filtered off and the filtrate was concentrated to yield 1-benzyl-4-[(5,6-dimethoxy-1-indanon)-2-yl] methyl piperidine free base which was redissolved in 100 ml methanol followed by addition of 10 ml methanolic—HCl (10%). The reaction mixture was cooled t 10° and the resulting solid was filtered and washed with cooled methanol.

Yield 13.16 g (92%). Mp 210–212°. ¹H NMR (200 MHz CDCl₃) δ (ppm) 7.4 (m, 5H), 6.9 (s, 1H), 4.0 (s, 3H), 3.9 (s, 3H), 3.5 (s, 2H), 3.2 (dd, 1H), 2.9 (d, 2H), 2.7 (m, 2H), 2.0–1.4 (m, 9H). Overall yield 95.5% (99%×92%).

EXAMPLE 3

4-[(5,6-Dimethoxy-1-indanon)-2-yl] methyl piperidine 10 g (0.035 mole) of 5,6-dimethoxy-2-(pyridin-4-yl) methylene indan-1-one and 1 g palladium on carbon (10%) were suspended in acetic acid (300 ml) at 50 psi and 75° C. for 4 hrs. Palladium was filtered off and the filtrate was concentrated. The residue was treated with 10% aqueous sodium hydrogen carbonate solution and the solution was extracted 3 times with dichloromethane (3×100 ml), dried over sodium sulphate and concentrated to dryness. Yield of 4-[(5,6-Dimethoxy-1-indanon)-2-yl] methyl piperidine was 10.1 g (99%). Corresponding HCl of 4-[(5,6-Dimethoxy-1-indanon)-2-yl] methyl piperidine had mp 248–250° C., lit. mp 249–250° C. (synthesis adopting different route of U.S. Pat. No. 4,895,841).

¹H NMR (base, 200 MHz CDCl₃) δ (ppm) 7.1(s, 1H), 6.9 (s, 1H), 3.9 (s, 3H), 3.8 (s, 3H), 3.0–3.2 (m, 3H), 2.6–2.7 (m, 4H), 2.2 (bs, 1H, exchanges with D₂O), 1.6–1.7 (m, 4H), 1.2–1.3 (m, 3H).

What is claimed is:

1. A process for the preparation of 1-benzyl-4-[(5,6-dimethoxy-1-indanon)-2-yl] methylpiperidine hydrochloride (Donepezil HCl) of the Formula I

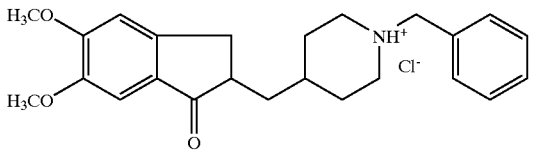

Formula I comprising hydrogenating 5,6-dimethoxy-2-(pyridin-4-yl) methylene indan-1-one with a noble metal catalyst or a non-oxide derivative of a noble metal catalyst in an organic solvent at 20–100° C. and 10–90 psi gauge pressure to form 4-[(5,6-dimethoxy-1-indanon)-2-yl] methyl piperidine of the Formula II

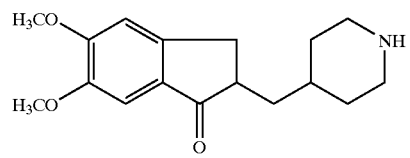

Formula II which is alkylated with an alkylating agent in an organic solvent at 20–80° C.

2. The process according to claim 1, wherein the organic solvent is selected from the group consisting of C₁–C₄ aliphatic alcohol, organic acid, ethyl acetate, aliphatic ketone, and mixtures thereof.

3. The process according to claim 2, wherein the organic solvent is acetic acid.

4. The process according to claim 1, wherein the noble metal catalyst is selected from the group consisting of palladium, rhodium, and ruthenium.

5. The process according to claim 4, wherein the noble metal catalyst is palladium.

6. The process according to claim 5, wherein the palladium is at 10% concentration.

7. The process according to claim 1, wherein the non-oxide derivative of a noble metal catalyst is a chloride or a sulphate of a noble metal selected from the group consisting of palladium, rhodium, and ruthenium.

8. The process according to claim 1, wherein the noble metal catalyst or the non-oxide derivative of a noble metal catalyst is supported on a carrier.

9. The process according to claim 8, wherein the carrier is selected from the group consisting of carbon, calcium carbonate, barium sulphate, and alumina.

10. The process according to claim 9, wherein the carrier is carbon.

11. The process according to claim 1, wherein the hydrogenation is carried out at 70–80° C.

12. The process according to claim 11, wherein the hydrogenation is carried out at about 75° C.

13. The process according to claim 1, wherein the hydrogenation is carried out at 45–55 psi gauge.

14. The process according to claim 13, wherein the hydrogenation is carried out at about 50 psi gauge.

15. The process according the claim 1, wherein the alkylation is carried out with benzyl bromide.

16. The process according to claim 1, wherein the alkylation is carried out in methylene dichloride and triethylamine mixture.

* * * * *